United States Patent [19]

Sideris

[11] Patent Number: 4,917,089

[45] Date of Patent: Apr. 17, 1990

[54] BUTTONED DEVICE FOR THE TRANSVENOUS OCCLUSION OF INTRACARDIAC DEFECTS

[76] Inventor: Eleftherios B. Sideris, 1600 Coulter, Suite 200B, Amarillo, Tex. 79106

[21] Appl. No.: 237,953

[22] Filed: Aug. 29, 1988

[51] Int. Cl.$^4$ ............................................. A61B 17/04
[52] U.S. Cl. .................................. 606/215; 128/899; 606/153
[58] Field of Search ............... 128/334 R, 334 C, 325, 128/899; 623/1, 12

[56] References Cited

U.S. PATENT DOCUMENTS

| | | | |
|---|---|---|---|
| 3,665,926 | 5/1972 | Flores | 128/326 |
| 3,786,816 | 1/1974 | Wolvek | 128/326 |
| 3,874,388 | 4/1975 | King et al. | 128/334 C |

OTHER PUBLICATIONS

Rashkind–Circulation–vol. 67, No. 4, Apr. 1983, pp. 711-716.

Primary Examiner—Dalton L. Truluck
Attorney, Agent, or Firm—Wendell Coffee

[57] ABSTRACT

A transcatheter occluding intracardiac defect device comprises a folding poly-urethane foam with Teflon coated wire skeleton, introducible into a long vascular sheath and automatically unfolded upon delivery in the distal to the defect cardiac chamber. A two mm string loop is attached to the center of the occluder, while the loop is closed by a 1 mm knot. A loading wire comprises a Teflon hollow wire and a double mono-filament thread which carries the occluder on the one end and is tied on the other end. An occluder-holder comprises a rhomboid poly-urethane foam with Teflon coated wire skeleton and a "rubber" piece sutured in the center. The occluder-holder is advanced over the loading wire axis and through the long sheath in the proximal to the defect cardiac chamber and is pushed against the occluder till it is securely buttoned. The distal end of the loading wire is cut and the hollow wire is pulled out over the double thread. The thread is pulled as a single strand and therefore the device is released.

3 Claims, 2 Drawing Sheets

BUTTONED DEVICE FOR THE TRANSVENOUS OCCLUSION OF INTRACARDIAC DEFECTS

BACKGROUND OF THE INVENTION

1. Field of the Invention

The present invention relates to an intracardiac prosthesis, and more particularly, concerns a transvenously deliverable prosthesis for the occlusion of intracardiac defects.

2. Description of the Prior Art

Intracardiac defects occur relatively uncommonly in children but can cause significant problems including congestive heart failure, pulmonary hypertension or even death. They are treated medically initially but quite frequently require surgical repair.

The surgical repair of intracardiac defects requires the use of general anesthesia, thoracotomy and heart-lung machine. It is associated with significant morbidity and mortality, pain for the child and a significant expense for the parents.

For these reasons attempts were made before to close intracardiac defects without surgery. For example see King et al U.S. Pat. No. 3,874,388.

The late Dr. Rashkind invented an umbrella device with hooks on the inside. The umbrella was introduced by a long catheter in the distal to the defect chamber it would open there and then would be pulled against the septal wall by the catheter till it was well hooked. Subsequently, it was released.

The method did not become popular, because it was associated with complications. Dr. Rashkind invented also a hookless two disk device. However details of the specifications are not known and none of the above devices was patented.

We know though a great deal more about his double disk device, designed to occlude a vessel called patent ductus arteriosus. There are hooks involved and a bulky delivery system, requiring a very large for a child long sheath(11F or 3.7 mm for a 17 mm device).

SUMMARY OF THE INVENTION

The intracardiac prothesis of the present invention provides the means of the transvenous, without surgery, occlusion of intracardiac defects. The occlusion is achieved by two independently buttoned components, the occluder and the counter-occluder or occluder holder.

In a preferred embodiment of the occluder aspect of this invention, the polyurethane form with the X shape wire skeleton is folded so that the skeleton wires become nearly parallel. Thus the occluder can be introduced through a 7F(2.3 mm) or an 8F(2.7 mm) long sheath. The foam has a diameter of 2 mm, while the wire is size 0.018–0.025". The wire is Teflon covered in order not to be thrombogenic.

The occluder is dipped into Heparin solution before the introduction. At the center of the occluder a 2 mm long double loop is attached. The loop is closed by a 1 mm diameter knot. In actuality this knot will be the "button" during the attachment with the counter-occluder.

Another aspect of the present invention is the counter-occluder, or occluder holder. It is rhomboid in shape, made also by 2 mm thick poly-urethane foam and a single 0.018" wire of equal diameter to the occluder. Foam and wire are stitched together by a continuously run suture. A 2 mm rubber piece of rhomboid shape is sutured at the center of the occluder-holder. By applying two sutures along the rubber piece, the foam is covering the rubber, so there is no friction during the introduction and the advancement of the occluder-holder in the long sheath.

A further aspect of the present invention is the release or loading wire. It comprises a Teflon coated hollow wire of a 0.028" wire and a double 0.005" Trilene thread, attached on the one end at already described occluder loop and tied on the other end of the hollow wire.

Trilene is a trademark and identifies a synthetic mono-filament fishing line or thread.

The loading or release hollow wire serves several purposes.

1. It is used to pull the occluder against the septum.
2. It is used to load the occluder-holder by threading the wire through the rubber center of the occluder-holder.
3. It is used as the axis of a pushing catheter and the long sheath, so the occluder-holder is pushed and is buttoned securely against the occluder.
4. It is used to release the device, by cutting its distal end, pulling the hollow wire over the double Trilene thread and then pulling the thread as a single strand.

In accordance with the principles of the present invention, the intracardiac prostheses hereof has significant advantages over known devices and specifically the Rashkind device and the King et al '388 device. It is miniaturized in size, requires a 7F(2.3 mm) or 8F(2.7 mm) sheath in comparison to a 15F(5.0 mm) sheath for the Rashkind device or a 23F(7.5 mm) sheath for a King et al device. It does not utilize hooks so it is not traumatic to the endocardium, or the conduction system. It conforms with the overall applicability of this intracardiac device to small children.

DETAILED DESCRIPTION

While this invention is satisfied by embodiments in many forms, will herein be described in detail a preferred embodiment of the invention, with the understanding that the present disclosure is not intended to limit the invention to the embodiment illustrated.

Figure 1:
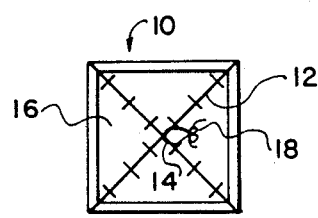
FIG. 1. is a perspective view of the preferred embodiment of the intracardiac prosthesis part of the occluder, illustrated in the unfolded condition.

Referring to the drawings, and FIG. 1 in particular, there is illustrated the preferred intracardiac prosthesis part, the occluder 10, of the present invention in the unfolded condition.

The occluder 10 is made by poly-urethane foam 16 lining 2 mm thick, with a diameter of 10 mm more than the diameter of the defect to be occluded. A Teflon coated wire skeleton 12 is introduced into the foam in an X shape and securely stitched to the foam by continuous and interrupted sutures.

A double loop thread or threaded loop 14 is securely attached at the center of the wire skeleton. The length of the loop is 2 mm and is closed by a knot of 1 mm in diameter.

Figure 2:
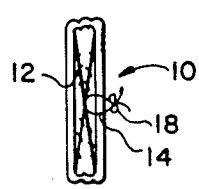
FIG. 2. is a perspective view of the preferred embodiment of the intracardiac prosthesis part of the occluder, illustrated in the folded condition, ready o be introduced in the long sheath.

In FIG. 2 which illustrates the occluder 10 folded, it becomes obvious how by applying gentle pressure on the edges of the wire skeleton between the thumb and the index finger, the occluder can be introduced into the long intravascular sheath 40. The long sheath can be as small as 7 or 8F in diameter so the device can be introduced through the vessels of small children.

Figure 3:
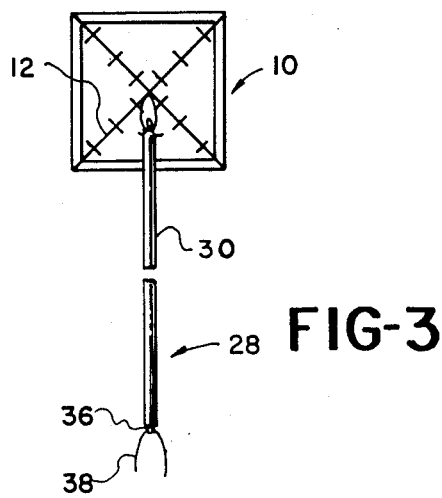
FIG. 3. is a perspective view of the occluder connected through the central loop with the loading wire.
Figure 6:
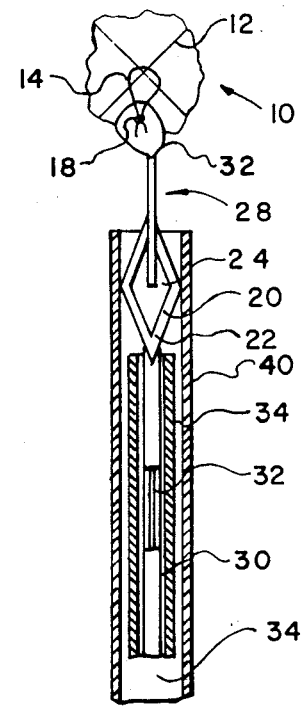
FIG. 6. is a cross-sectional view of the intracardiac device part of the occluder-holder as it is introduced into the long sheath, over the loading wire.

Turning now to FIG. 3, the occluder 10 is connected to loading wire 28. The loading wire 28 consists of hollow wire 30 of a 0.028" Teflon coated wire and the double 005" Trilene mono-filament thread 32. The mono-filament thread 32 is passed through the "button" loop 14 attached to the occluder 10 and then through the hollow wire 30 in a double fashion. (FIGS. 3 and 6)

Mono-filament thread 32 is tightened several times at distal end 36, of the loading wire 28, so it is stretched inside the hollow wire 30.

A 3 cm thread end 38 is left after the knot at the distal end 36 in the mono-filament thread 32, to facilitate the future introduction of the occluder-holder 20 over the wire 28.

The loading wire 28 serves several purposes as it has been described before, pulling the occluder-10 against the septum, serving as the loading axis of the occluder-holder 20 and finally incorporating the release mechanism of the intracardiac device.

Figure 4:
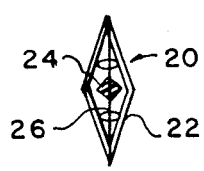
FIG. 4. is a perspective view of the intracardiac prosthesis part of the counter-occluder or occluder holder.

FIG. 4 describes the occluder-holder 20 which is also made by 2 mm thick foam 22. The length of the occluder-holder 20 is selected as equal to length of the occluder 10. Skeleton 26 is made by 0.018" Teflon coated wire to avoid clot formation. Wire 26 and foam 22 are stitched together by continuous and interrupting sutures.

On the center of the occluder-holder 20 a 2 mm rubber rhomboid rubber piece 24 is sutured. It serves several purposes. Firstly allows the occluder-holder 20 to be moved on the loading wire 28 axis without danger of dislodgement. Secondly it has elastic properties, so it is distended to allow the button knot 18 through. Thirdly it serves as the button-hole, so that it does not allow the knot 18 to un-button after detachment, thus holding the occluder 10 and occluder-holder 20 together.

Two stitches sutured along the rubber button allow the rubber 24 to be covered by foam 22. Thus, the friction is minimized during the introduction and the advancement into the long sheath 40.

Figure 5:
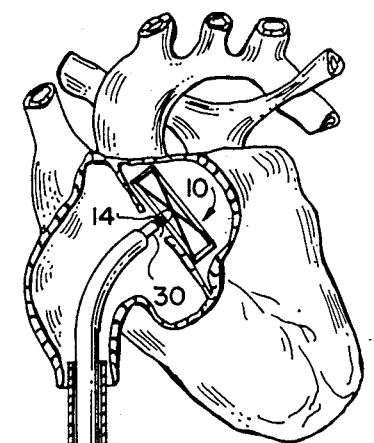
FIG. 5. is a cross-sectional view of the intracardiac device part of the occluder, connected to the loading wire and occluding an atrial septal defect.

FIG. 5 describes the introduction and the positioning of the occluder 10 inside the heart. The folded occluder is introduced as described before into the long sheath 40. A 7F end-hole catheter 34 is introduced over the loading wire 28 into the long sheath 40 and it is pushing the occluder 10 till it exits in the cardiac chamber distant to the cardiac defect. After the occluder 10 comes out from the long sheath 40, it is automatically unfolded and pulled gently with the loading wire 28 against the septal wall where the occluder is loosely attached.

FIG. 6 describes the introduction of the occluder-holder 20 inside the long sheath 40. The loading wire 28 is threaded through the center of the rubber piece 24 of the occluder-holder. The occluder-holder 20 is then advanced over the loading wire 28 and it is introduced into the long sheath 40 . The 7-F end-hole catheter 34 is introduced over the loading wire 28, pushing the occluder-holder, till it exits the long sheath 40 in the proximal to the defect cardiac chamber.

Figure 7:
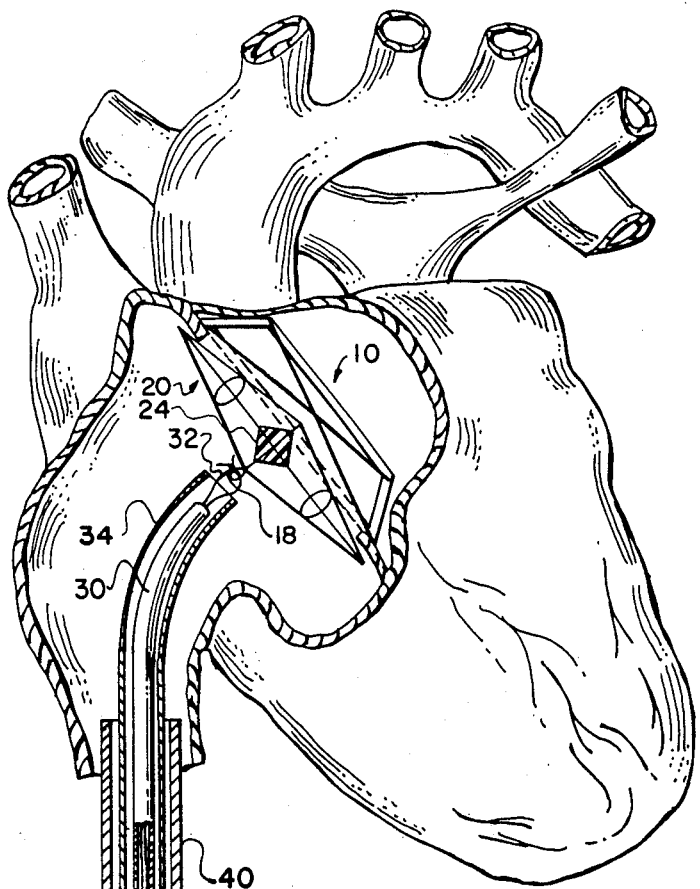
FIG. 7 is a cross-sectional view of the occluder and occluder-holder parts of the device buttoned together and occluding the atrial septal defect.

FIG. 7 illustrates the attachment of the occluder 10 to the occluder-holder 20. The occluder-holder has exited the sheath 40 and is pushed by the end-hole catheter 34 in a parallel fashion to the defect and the occluder, but still on the loading wire 28 axis. The loading wire is pulled gently, while the occluder-holder 20 is pushed by the end-hole catheter 34 and the end of the sheath 40. The actual "button" process involves the entry of the knot 18 of the occluder loop 14 into the rubber center 24 of the occluder-holder and the attachment by the "valve" like action.

Figure 8:
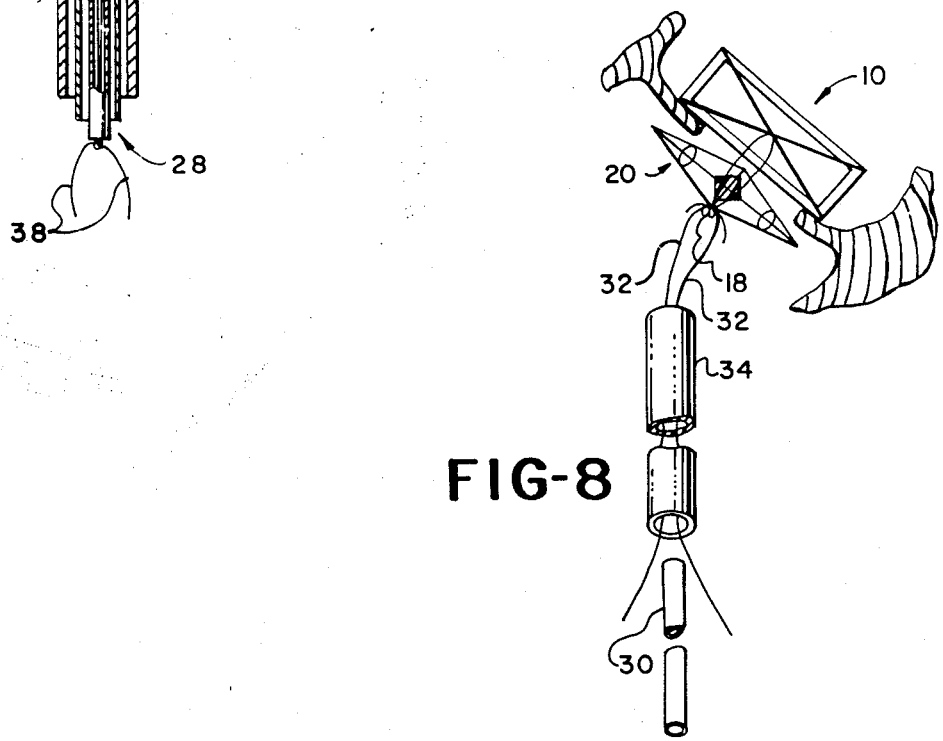
FIG. 8. is a cross-sectional view of the detachment of the intracardiac device in the heart and removal of the loading wire and the long sheath.

FIG. 8 illustrates the detachment. The end of the loading wire 28 is cut. A sterilized pair of small pliers is used to cut the end of the hollow wire 30 and the tightened double 0.005" mono-filament thread 32 which are located outside the body. Thus they become detached from each other and they are removed with the following mechanism: The hollow wire 30 is pulled out over the double 0.005" mono-filament thread 32. The thread 32 is subsequently pulled out as a single strand, so that the device is detached inside the heart after the defect is occluded.

The present invention provides a percutaneous deliverable intracardiac prosthesis, suitable for treatment of various intracardiac defects, including atrial septal defect, ventricular septal defect and cardiac defects as parts of more complex lesions.

As an aid to correlating the terms of the claims to the exemplary drawing, the following catalog of elements and steps is provided:

10 occluder
12 skeleton
14 thread loop
16 polyurethane disc
18 knot
20 counter-occluder or occluder holder- rhomboid
22 polyurethane disc - (holder)
24 rubber piece - rhomboid
26 skeleton
28 loading wire
30 hollow wire or tube
32 Trilene thread
34 catheter
36 Distal end
38 Thread end
40 long sheath

I claim:
1. An intracardiac percutaneously deliverable device for the repair of heart defects comprising:
  a. an occluder, said occluder including:
    i. a foldable foam polyurethane disc with
    ii. a Teflon coated wire skeleton in the form of an "X" sutured to the foam disc, and
    iii. a thread sutured to the center of the wire skeleton, iv. said thread formed into a loop with
v. a knot closing the loop remote from the skeleton,
b. an occluder-holder, said occluder-holder including:
 i. a foldable foam polyurethane rhomboid disc with
 ii. a single wire skeleton sutured to the rhomboid disc, and
 iii. a rubber piece sutured at the center of the rhomboid disc,
c. a loading wire including:
 i. a Teflon coated hollow wire, and
 ii. a long thread,
d. said loading wire pierced through an opening in the occluder-holder and its rubber piece,
e. said long thread extending
 i. through the hollow wire,
 ii. through the thread loop at the occluder, and
 iii. back through the hollow wire;
f. so arranged and constructed that
 i. the occluder-holder may be pushed toward the occluder and
 ii. pulling on the loading wire will pull the knot through the rubber piece on the occluder-holder thereby
 iii. buttoning the occluder-holder to the occluder.
2. The process of occluding a defect in a heart in which
a. an occluder is placed on one side of the defect and and
b. an occluder-holder is placed on the other side of the defect;
c. wherein an improved method of connecting the occluder and occluder-holder comprises:
d. before placing the occluder in the heart
 i. attaching a loop of thread to the occluder,
 ii. knotting the loop, and
 iii. piercing the occluder-holder,
e. then after placing the occluder and occluder-holder in place
 i. pulling the knot through the pierced occluder-holder thereby
 ii. buttoning the occluder to the occluder-holder.
3. The invention as described in claim 2: wherein
f. said occluder-holder is pierced by a loading wire which
g. is used to place the occluder-holder,
h. then after the occluder holder is buttoned to the occluder:
 i. cutting the loading wire,
 ii. removing the loading wire, and
 iii. removing a long doubled thread extending through the loop on the occluder by
 iv. pulling one end of said doubled thread.

* * * * *